(12) United States Patent
Braun et al.

(10) Patent No.: US 8,799,811 B2
(45) Date of Patent: Aug. 5, 2014

(54) METHOD AND APPARATUS FOR DISPLAYING MEDICAL THUMBNAIL OBJECTS IN A BROWSING COMPONENT

(75) Inventors: Christoph Braun, Rosenheim (DE); Martin Kessner, Munich (DE); Petra Rummel, Frankfurt (DE)

(73) Assignee: Siemens Aktiengesellschaft, Munich (DE)

(*) Notice: Subject to any disclaimer, the term of this patent is extended or adjusted under 35 U.S.C. 154(b) by 916 days.

(21) Appl. No.: 12/335,573

(22) Filed: Dec. 16, 2008

(65) Prior Publication Data
US 2010/0050114 A1 Feb. 25, 2010

(30) Foreign Application Priority Data
Aug. 22, 2008 (EP) .................................. 08014919

(51) Int. Cl.
*G06F 3/048* (2013.01)
*G06F 3/0481* (2013.01)
*G06F 3/0485* (2013.01)

(52) U.S. Cl.
USPC ............ 715/788; 715/815; 715/833; 715/838

(58) Field of Classification Search
CPC ...... G06F 3/048; G06F 3/0481; G06F 3/0485
USPC ................... 715/788, 810, 815, 835, 838, 833
See application file for complete search history.

(56) References Cited

U.S. PATENT DOCUMENTS

| | | | |
|---|---|---|---|
| 7,391,423 B1* | 6/2008 | Manzari et al. | 345/619 |
| 8,132,116 B1* | 3/2012 | Schendel | 715/764 |
| 8,510,669 B2* | 8/2013 | Schiller | 715/769 |
| 2003/0076361 A1* | 4/2003 | Hatanaka et al. | 345/771 |
| 2005/0060665 A1* | 3/2005 | Rekimoto | 715/810 |
| 2005/0108655 A1* | 5/2005 | Andrea et al. | 715/798 |
| 2007/0089061 A1* | 4/2007 | Terada | 715/723 |
| 2007/0186189 A1* | 8/2007 | Schiller | 715/838 |
| 2007/0253025 A1* | 11/2007 | Terayoko | 358/1.16 |
| 2008/0109796 A1* | 5/2008 | Kosche | 717/158 |
| 2008/0126958 A1* | 5/2008 | Louie | 715/764 |
| 2008/0148183 A1* | 6/2008 | Danninger | 715/810 |

* cited by examiner

*Primary Examiner* — Daeho Song
(74) *Attorney, Agent, or Firm* — Schiff Hardin LLP

(57) ABSTRACT

A computer-implemented method and a system for browsing medical thumbnail objects to be displayed on a window on a monitor before loading the medical objects. It is possible to load only those images which indeed are relevant for a user and thus to save transmission time. A display pattern for displaying the thumbnail objects is user-selectable and includes a number of objects to be displayed and advantageously the arrangement or pattern remains constant, even in case a window size has been modified. Using a fixed but user-selectable layout pattern supports selection of relevant images during browsing. The window size is also user-selectable. After having determined the display pattern and the window size the size of the thumbnail objects is calculated automatically according to the determined display pattern and the determined window size. The thumbnail objects are displayed in the calculated object size, which favorably simplifies browsing of complex medical images.

6 Claims, 6 Drawing Sheets

METHOD AND APPARATUS FOR DISPLAYING MEDICAL THUMBNAIL OBJECTS IN A BROWSING COMPONENT

BACKGROUND OF THE INVENTION

1. Field of the Invention

The present invention relates generally to method and apparatus for a graphical user interface in medical imaging. In particular, the present invention provides a method and apparatus for browsing thumbnail images of medical objects to support selection of relevant medical data to be selected and reviewed for clinical assessments and other purposes before loading the medical objects.

2. Description of the Related Art

Medical personnel regularly work with and review medical data such as medical image data. This medical data may be viewed on a variety of devices and systems, resulting in the same data being displayed in different ways on different devices. Clinical applications are usually based on distributed systems that are interconnected by one or more networks. Medical users typically work with patient data on a user component of the system (where the user component acts for example as a client), while the data is stored on another component of the system (for example the data is stored on a server). For clinical and other purposes, medical users browse through a plurality of medical data sets and make a choice of which images should be loaded and displayed (for example on the client machine or other user component). The set of data being reviewed is usually represented on a display by graphical objects or by means of a list that are displayed to the user on the display panel or screen of the client machine or client component. If the medical data being reviewed is radiological data, for some radiological images the user can make a choice from among the data with greater ease if the data is depicted as thumbnail images, or so-called thumbnails, of the images. For other images or data, a list of the data would be more informative to the user in making a selection than a thumbnail image. Sometimes both types of information needs to be considered alternatively by the user to make a choice as to which data is to be loaded and displayed.

In medical imaging, different imaging techniques (for example ultrasound imaging and magnetic resonance (MR) imaging techniques and the like) result in different types of image data as the output. Depending on the image type and depending on the clinical use case, different requirements arise as to how to display the data in order to provide optimal support for the chosen image data in a browsing or display application. For example, a comparison between the different images has to be made. The system has to supply sufficient information to the user to distinguish the data. Due to the fact that some of the medical data consists of huge volumes of data, which in turn leads to long loading times, it is helpful to be able to select the relevant data before the image data is loaded from storage to the display device.

Moreover, the user has to take into account a huge number of different types of information with respect to the specific clinical use case. Therefore, it is necessary that a general display pattern as a structure for displaying the medical data remains constant. Since radiological image acquisition follows well known procedures, users also take into account information regarding the sequence and the position of the images and of items of medical information that may be associated with the medical data, or image data, when searching for the target data, for example, to be reviewed in detail. Therefore, any change in the underlying structure for the display of the medical objects is a disadvantage for the user.

Additionally, medical applications run on various devices with different technical conditions (for example the devices may have different screen sizes and monitor resolutions or different video driver systems). A fixed setting such as the item size or the number of medical objects to be displayed can create a mismatch between the technical display capabilities of the specific device and the actual display of items for the purpose of browsing the display items.

In the state of the art, various systems and methods are known for viewing pictures. However, with respect to medical imaging, known graphical applications do not fulfill the display requirements for browsing medical image data sufficiently. In particular, it is not possible to control an image size of the medical objects and the number of the medical objects separately.

A freeware program called "Irfan View" displays various image formats. This program provides controls or settings for thumbnail size in pixels to determine a display size. The number of thumbnail images that will be displayed usually cannot be controlled directly.

In particular and with respect to medical imaging, it is helpful that the objects to be displayed are displayed in a structure or arrangement which remains constant even in case of adjusting of the window size in which the objects are to be displayed. Moreover, it is necessary that a user is able to get more detailed information with respect to the object to be displayed before loading the object into the user machine or client component. Therefore, it would be a drawback if the objects were to be displayed in a fixed manner, namely without the possibility to adjust the number of items to be displayed and the size of the items in the display.

Therefore, there is a need for providing a method for displaying medical objects for the purpose of browsing the objects which includes an augmented functionality with respect to display capabilities. It should be possible that a user is able to make a more dedicated choice with respect to displaying medical objects. In other words, the user should be able to select the display setting that better meets the user's needs. Further, it should be possible to control the number of medical objects that are to be displayed and to control the size of the medical objects to be displayed separately, while maintaining a general display pattern for displaying the medical objects. Moreover, controlling of the size and the number of objects should be made as simple as possible. In particular, the number of control units for adjusting the display parameters should be minimized.

SUMMARY OF THE INVENTION

The present invention provides a method for displaying medical image objects as thumbnail objects on displays of various medical devices and client devices. The invention also provides an apparatus, including a system as well as a software product stored on computer readable media, for displaying the thumbnail objects that provide the advantages described herein.

In the following the present invention is described in relation to the method. The system and the computer readable medium or the computer program product of the invention incorporates one or more of the features that are described in relation to the description of the method. Any functional feature described with respect to the method can also refer to a module of the system, having a particular functionality. For example the method step of "displaying" can also refer to a "display" or "display unit" which might be incorporated in a graphical user interface and which is adapted to display objects on a monitor or display panel.

In particular, the present invention relates to a computer-implemented method for browsing medical objects which are displayed as thumbnail objects or other types of medical objects to be displayed in a window portion of a computer display, represented on a monitor which serves as a graphical user interface, comprising the following steps:

determining a display pattern for the objects, wherein the display pattern is constitutive for a number of objects;

automatically calculating the size of the objects to be displayed according to the determined display pattern and according to a determined window size; and displaying the objects on the graphical user interface in the calculated size for the purpose of browsing by a user.

The following are definitions of selected terms employed herein.

The term "medical objects" refers to any type of data that is used in or that is relevant in the medical field, and can include radiographic images, ultrasound images, sonogram images, photographs, and other image data, as well as tables, charts, lists, text, patient records, sound data, video data and the like. Depending on the specific use case it is also possible to have a combination of the types of data mentioned above as medical objects. A preferred embodiment of the present invention is used in the medical field. However, it is also possible to apply the invention in other fields of technology. Then, the displayed objects are not necessarily objects used in the medical field and are related to another content. As such, the term "medical objects" is not limited to objects in the medical field. Generally, the objects represent data or items of data and include thumbnail images of the objects, which usually are employed if there is a focus on a proportion of data (referring to a DICOM-standard: the series).

The term "window" refers to an element of a graphical user interface to be depicted on a monitor of a computer. Generally, the window will define an area of the graphical user interface and typically will be outlined with a border. The medical objects to be displayed are shown in a window for the purpose of browsing. The (browsing) window is adapted to display all of the relevant information that the user may find necessary for the purpose of selecting the relevant objects before loading the selected objects into the user machine or client computer. Therefore, in a preferred embodiment a window is part of a container, wherein the container acts as an accumulative window for several windows. The container is adapted for displaying several windows, which each comprise elements for displaying medical objects and fields for displaying meta-information. The meta-information for example might include an indication of a data source, a "patient field" that provides identifying information about the patient, a "studies field" that, for example, identifies any related studies and an "information field"

Further, the window includes a control for user interaction. The control of one embodiment is a control bar. The control bar for example may have a slider control for determining the display pattern for the objects to be displayed in the window in response to the user interaction.

In some embodiments, the window might be adapted to incorporate other sections and other fields for further information. Additionally, it is possible that the container only consists of one window for displaying the medical objects. Also, the window might comprise sub-windows for displaying different categories of information. In case the window size is adapted or adjusted according to the method of the invention, the size of the frame and/or of the sub-window is automatically adjusted based on the adaption or change in the window size. Further, it is possible to apply the concept of the present invention not only to the window as such, but also to the frame incorporating the window and/or to the sub-window within the window. In this case, the term "window" should be construed as including a "window," a "frame" or "sub-window" or "container for windows" respectively, wherein the frame comprises at least one thumbnail object and wherein the sub-window is part of the window for displaying thumbnail objects and wherein the container comprises at least one window. Further, the windows might be nested. In this case the outer window forms a container for displaying images. The container is resizable itself within the surrounding frame.

The term "display pattern" refers to the layout for displaying the medical objects in the window. Typically, the display pattern is a fixed set of square layout grids, for example, the display device may show 1, 2, 4, 8 or 16 thumbnails as selected by the user. The arrangement of the thumbnail images within the layout is fixed, unless the user changes the arrangement directly. In other embodiments, other numbers of thumbnails might be chosen for display. For a person skilled in the art, it is apparent that other layouts may be specified (for example in a circular shape or in form of a linear arrangement or rotating display or the like). Generally, the display pattern that has been selected is decisive for the number of objects that will be displayed. In this respect, the layouts can be considered as configurations on how to display images or objects to help selecting the correct data for loading. The corresponding control for selecting a specific layout is a slider. The user can operate this control to make a direct change in the layout; otherwise the layout remains unchanged. And more importantly, the position of the displayed thumbnail images within the layout remain unchanged. This avoids the confusion that might be caused if the thumbnail images moved position, for example moved from one row to another, when changes are made to other aspects of the display, such as a change in the window size. The system automatically takes care that all objects are fully visible by choosing the correct object size for displaying the objects in the layout, preferably in a non-overlapping manner.

The terms "pre-definable," "pre-defined," or predetermined is to be construed in that it is possible to define or determine the parameters, items or configurations in a preparation phase. For example, there might exist a pre-defined set of items, and from the set of items the user might select one item to be applied. Further, it is possible that the user makes an input for designing the parameters to be applied. Normally, definitions and pre-definitions are made in the preparation phase which takes place before an execution phase. In a preferred embodiment of the invention, a method is provided wherein the steps of determining the display pattern and determining the window size are executed in the preparation phase, whereas the steps of calculating and displaying the objects are executed in the execution phase. However, it is also possible that the steps of determining the display pattern, determining the window size, calculating the size of the objects and displaying the objects are executed in the execution phase.

Further, another sequence of the method steps is possible. In particular, it is possible to execute the step of determining the window size before executing the step of determining the display pattern.

According to one aspect of the present invention, a display pattern is selectable in response to a user input. In case the display pattern is modified or adjusted, the updated display pattern is used for further processing (in particular, for calculating and displaying). This is done automatically. A modification or adaption of the display pattern is possible at every point in time. That is to say, for example during the displaying of the objects it is possible for the user to select another display pattern by direct input. In the latter case, the displaying process is stopped and the displaying step is calculated on the basis of the adapted display pattern. No further user interaction is necessary. As an advantage, the user gets more flexibility in controlling the display of the medical objects.

According to a preferred embodiment of the present invention, the window size is continuously scalable or is scalable in pre-definable increments upon receipt of a user input so that, in general, the window size is always adaptable or modifiable. In case the window size has been changed by the user, the displaying step is based on an automatically updated window size. The change leads to an automatic adaption of the object size by retaining the determined display pattern. Normally, the window size is pre-defined (and preferably is set at full screen, although other settings are possible). However, it is also possible that the window size is determined upon a user input (for example by the user dragging the uppermost edge or bottom of the window). It is also possible that the window size is changed without user interaction. This might be the case, if context conditions (which might be represented by a set of operating system parameters) make it necessary to adapt the window size automatically. For example, it might be necessary to adapt the size of the window to a particular device on which the window will be displayed, due for example to the device having a larger or smaller display screen. According to a preferred embodiment, any change with respect to the window size triggers a calculation of the object size while retaining the determined display pattern as a constant.

According to yet another aspect of the present invention, determining the display pattern is triggered by a user input, or in an alternate embodiment a display pattern is determined by selecting a specific display pattern from a pre-defined set of display patterns provided on a graphical user interface. Normally, the graphical user interface comprises an interactive element in form of a grid in which the number of objects to be displayed might be selected. According to another aspect of the present invention, determining the window size is triggered by a user input. That is to say, as soon as the user inputs any change with respect to the window size (for example when the user performs a drag or slide operation of the slider control via a computer mouse or the like) the further processing steps (calculating, displaying) are based on the updated window size. Normally, such a window size is pre-defined as that which fits best to the typical medical applications. With this embodiment usability of a browsing component is enhanced.

According to another embodiment of the present invention, determining the display pattern is executed separately from determining the window size. Usually, the display pattern is determined by a user interaction. Another independent and separate user interaction is constitutive for determining the window size. If there is no user interaction for changing the pre-defined window size, the calculation is based on the pre-defined window size. In this embodiment the user gets more flexibility to adapt displaying of thumbnail objects more specifically according to the present clinical use case.

According to a further aspect of the present invention, the display pattern is based on a pre-defined matrix-like grid structure and wherein a display pattern is user-selectable by using a slider-type graphical element as the control for specifying a specific display pattern as selected. The slider control is an element of the graphical user interface associated to the window and acts as the control element for the display pattern. The slider control element controls the displaying step of the thumbnail objects. With this aspect a user is provided with an easy to manipulate mechanism for controlling the graphical representation with a minimum of user interactions being necessary.

In another advantageous embodiment of the present invention, the display pattern is not determined by a user input, but is determined automatically. First, a type of data of the objects to be displayed is determined. Based on the type of data (for example medical images from different imaging modalities, clinical examination types, textual data and the like) the display pattern is determined automatically, based on pre-defined rules. The rules are set in the preparation phase and specify a most suitable display pattern for a set or a combination of objects with respect to their type (for example a possible rule is "angiography examination ->2×2 layout grid pattern")

Using fixed, typical layout patterns for viewing the medical image objects will support the selection task since an appropriate layout pattern for the task at hand can be chosen directly.

Another feature and advantage of the present invention is that the window size can be adjusted to different monitor sizes and screen resolutions to obtain an optimal use of screen real estate available. This is especially relevant as medical systems comprise a plurality of different client computers with different system parameters such as different monitor sizes, etc. An automatic adaption of the display to the monitor at hand is possible. A further advantage of the present invention is that there is no resorting of the thumbnail images during an object selection process, even in the case where the display pattern and/or the window size are changed. The structure of the medical objects to be displayed within the windows (e.g. their image position) remains constant. This increases usability and efficiency, particularly in complex systems.

With the inventive design for displaying thumbnail objects, it is possible to control the object size and the number or amount of objects separately. Those parameters, mentioned before, can be controlled independently. Further, the function to change the object size and the function to set the number of the objects to be displayed may be combined into one control. The control allows the user to choose a reasonable number of objects which is linked with a display size of the objects. According to a preferred embodiment mentioned above, this is achieved with a set of layout grids. By choosing a certain number of objects the size of objects is also pre-determined. Moreover, the size of the objects can be dynamically regulated indirectly by resizing the window.

Due to the scalability of the window size, the object size can be manipulated independently from the number of objects by resizing the browser window. Changing the window size does not deliberately alter the number—and arrangement—of objects, which yields a better ability to control displaying of objects in the browsing component. In this respect it is important that not every change of the browser window leads to a change of object size. The size of the objects in a so-called content area is generally determined by the size of the objects at the shorter border of a frame of the respective window.

The present invention refers provides a computer-readable medium having stored thereon instructions that are executable on a computing device for browsing medical objects, wherein the instructions are adapted to execute the method as described herein.

Further, the invention relates to a system for browsing medical objects, in particular thumbnail objects, which are to be displayed on a window on a monitor. The system comprises a computer in communication with the monitor for displaying a graphical user interface, a browser for browsing the displayed objects according to a method as described herein and a user interface for detecting user input in order to control the displaying of the objects on the monitor.

DETAILED DESCRIPTION OF THE PREFERRED EMBODIMENTS

The preferred embodiments provide a method for browsing thumbnail objects to be displayed in a window on a monitor or display in a non-overlapping manner are described herein after. One skilled in the art will recognize, however, that the invention can be practiced without one or more of the specific details, or with other methods, modules, entities, etc. Well-known structures, computer-related functions or operations are not shown or described in detail, as they will be understood by those skilled in the art.

Further, the method provides for displaying of thumbnail objects. However, other categories of objects might also be applied, processed, and displayed, respectively. Furthermore, the particular features, structures or characteristics may be combined in any suitable manner in one or more embodiments.

Figure 10:
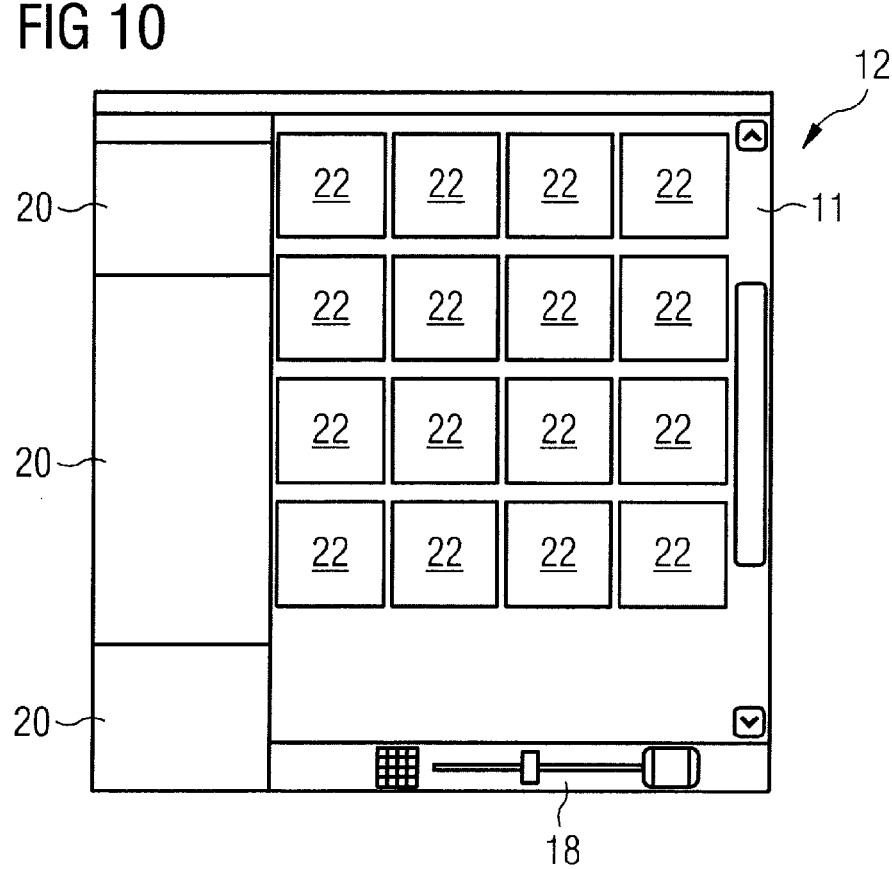
FIG. 10 is a schematic illustration of the window of FIG. 9 after vertical enlargement according to a preferred embodiment of the present invention.
Figure 11:
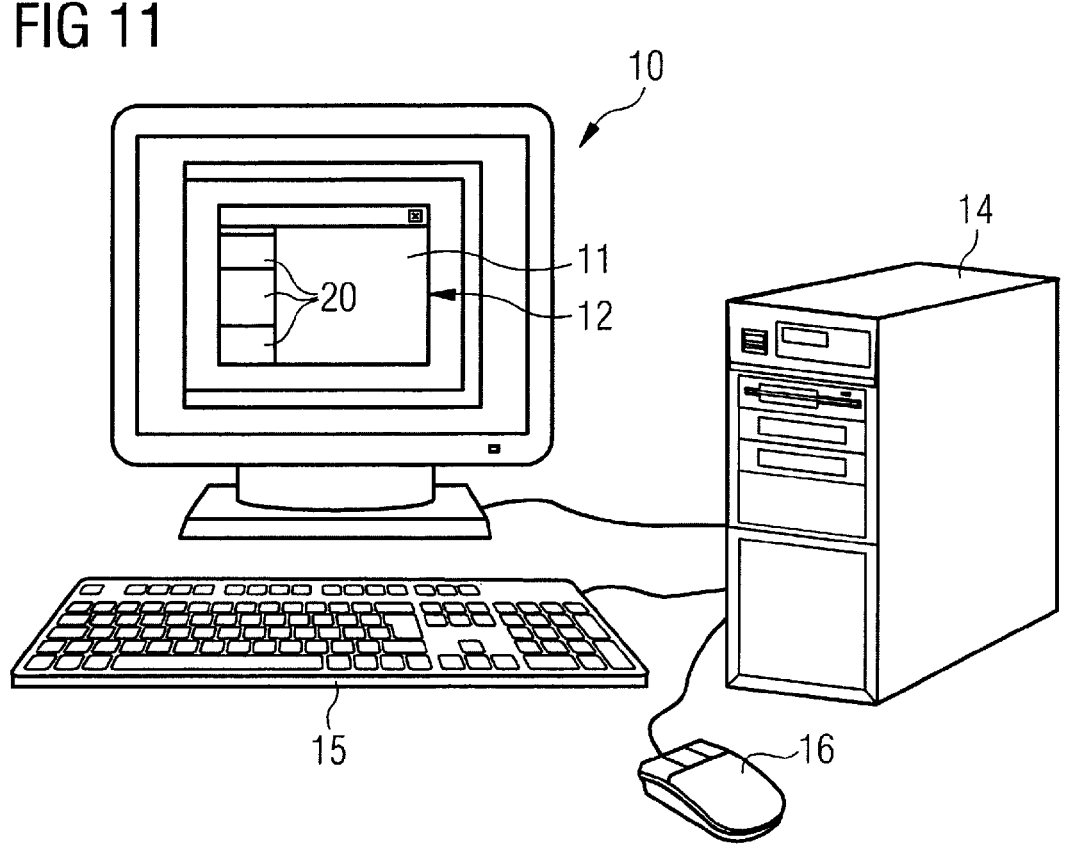
FIG. 11 is a perspective view of a computer system with a monitor for browsing medical objects according to a method of a preferred embodiment of the present invention.

With reference to FIG. 11, the present invention may be implemented as a computer-implemented solution for browsing medical thumbnail objects 22 (shown in FIGS. 1-10) to be displayed on a window 12 on a monitor 10 of a computer 14 before loading the medical object 22 into the computer 14, such as from a network server. The structure of the computer system depicted in FIG. 11 is but one example of a computer that may implement the method. Other computers or computer displays may be provided as display panels on medical devices or other devices, flat panel or CRT displays or monitors remote from a computer, projection displays, and all other such display means. The illustrated computer 14 includes the monitor 10, a keyboard 15 and a computer mouse 16 or other pointing device. The monitor 10 is adapted to display medical thumbnail objects 22 for the purpose of browsing and is related to a browser of a browsing component or application. The browser is a software program or module that is executed by the computer, or by a computer remote from the display. The window 12 is a graphical element displayed on the monitor 10 and includes a frame 11 within which is displayed the thumbnail objects 22 and may include other fields or elements 20 for displaying meta-information for the thumbnail objects 22 to be displayed. The frame 11 is a all-embracing area for all thumbnail objects 22 within the window 12.

A thumbnail object 22 is a downsized, minimized version of the respective object that the thumbnail refers to or represents. A thumbnail object 22 serves as an index for or a pointer to the object. For objects that are medical images, the thumbnail object 22 is a size-reduced representation of the medical image data, like radiological images or images of an angiographic examination or of another modality. A thumbnail object 22 might comprise 2D-, 3D- and 4D-data.

Figure 1:
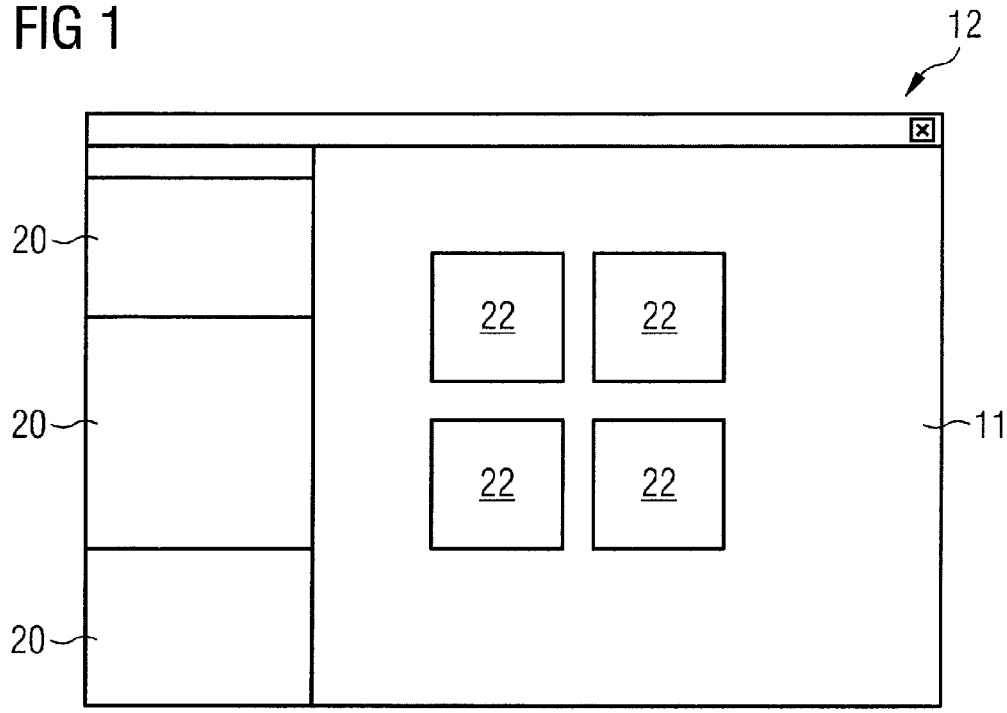
FIG. 1 is a schematic illustration of a window portion of a computer display for displaying thumbnail objects according to a preferred embodiment of the present invention.

With respect to FIG. 1, a general structure of a browser graphical display component according to the present invention is depicted in more detail. In particular, the window 12 is shown with the elements 20 for displaying meta-information and with the frame 11 for displaying the thumbnail objects 22. As can be seen in FIG. 1 the window 12 comprises three elements or areas 20 for displaying meta-information. Meta-information of one embodiment includes additional data that is related to or provides background information for the image data. The three elements 20 depicted in FIG. 1 for display of the meta-information in one example refer to patient-related data, studies data, and general information. General information for example can include a time of acquisition of image data, a context of acquisition of data or technical acquisition parameters or the like. Meta-information of another example includes time of acquisition of the image data, context of acquisition of the image data and further technical or non-technical parameters with respect to the image acquisition. Other elements 20 are used for depicting patient related data and study related data for the respective series or studies shown on the right hand side of the window 12 by the thumbnail object 22.

Usually, the elements for displaying meta-information 20 are ordered on the left hand side of the window 12, whereas thumbnail objects 22 are shown in the frame 11 on the right hand side of the window 12, which covers most of the window 12. These elements can be arranged in other ways. However, an advantage is realized for the user when a given arrangement is presented and other displays retain this arrangement. The general structure of the window 12 according to preferred embodiment of the present invention of the user interface model can be adapted according to the specific and actual use case. For a person skilled in the art it is obvious that the structure might be adapted to other use cases or preferences, so that for example the frame 11 might be shown on the left side, whereas the elements 20 might be shown on the right. Other arrangements of the image elements are also possible.

As can be seen in the example depicted in FIG. 1, the window 12 consists of four major application areas:

a navigation area,
an information area which is depicted on the left hand side in FIG. 1, which in the illustrated embodiment consists of three elements 20 (e.g. patient-related information, study-related information and general information),
an on-demand information area, and
a content area (which in a preferred embodiment of the invention is represented by the frame 11) in order to represent series of multi-frame thumbnails 22 or alternatively a list or series or multi-frames.

Figure 2:
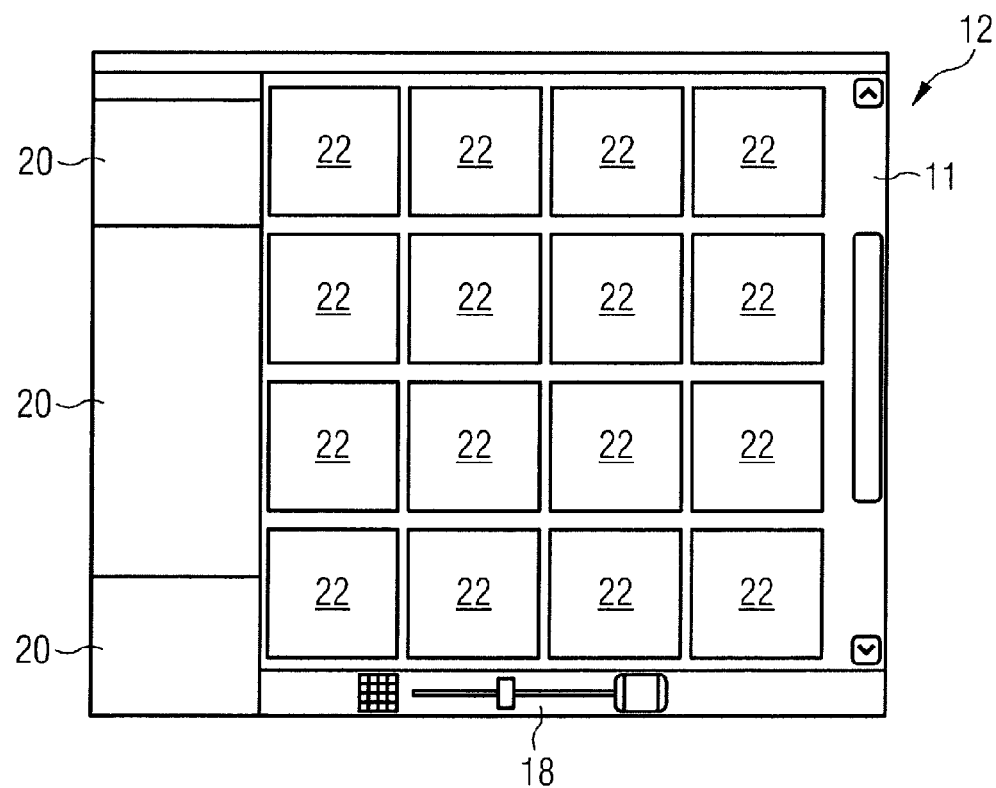
FIG. 2 is a schematic illustration of a window portion of a computer display with a slider control unit for selection of the display pattern according to a preferred embodiment of the present invention.

With respect to FIG. 2, the window 12 is shown in more detail. In FIG. 2 the window 12 comprises a slider graphical element 18 for controlling the display of thumbnail objects 22. The slider control 18 is arranged at a bottom side of the window 12. The slider 18 includes a slider handle as a graphical element that is operated by the user by sliding or dragging the graphical element depicting the sliding element as a user interaction. The slider 18 also might comprise a graphical increment element for incrementally changing a display pattern. For example, a number of buttons might indicate how many thumbnail objects 22 are to be displayed in the window 12. A further element of the slider 18 might be a graphical element in which numbers might be inputted by a user interaction. For example, in this field a user might input the number '16'. Accordingly, sixteen thumbnails 22 would be displayed in the window 12. An additional element of the slider 18 might be a preview area. The preview area is a small representation of the layout pattern which has been selected by the user, shown for example as an arrangement of small squares. The preview is automatically adapted if a modification with respect to the layout pattern is detected. FIG. 2 shows—by way of example—a window 12 which comprises a 4×4-layout pattern. Thus, sixteen thumbnail objects 22 are displayed in the window 12.

Generally, if the size of the frame 11 is changed in response to a user input (for example by the user performing a drag operation using the mouse 16 at the edge of the frame), then automatically the size of the thumbnail objects 22 is calculated again, based on the amended size of the embracing frame 11. The same holds for a change in the size of the window 12 in response to some other user input. Also in case of an amended window size 12 the size of the thumbnail objects 22 within the window 12 is calculated again and the calculation is performed automatically. Thus, according to a preferred embodiment the size of the thumbnail objects 22 is only changeable indirectly via changes in the window size, changes in the frame size or a change of the selected display pattern. There is no user control for changing the size of the thumbnail objects 22 directly.

In the following, embodiments shown in FIGS. 3 to 10 are described, wherein the window 12 of the browsing component is shown in different conditions, which includes an illustration before and then after a modification of the window size. In these examples the change in the size of the window 12 (or the frame 11) is only executed in one direction (vertical or horizontal). Other examples refer to a change in both directions. This leads to another adaption or change of the display for the objects 22.

Figure 3:
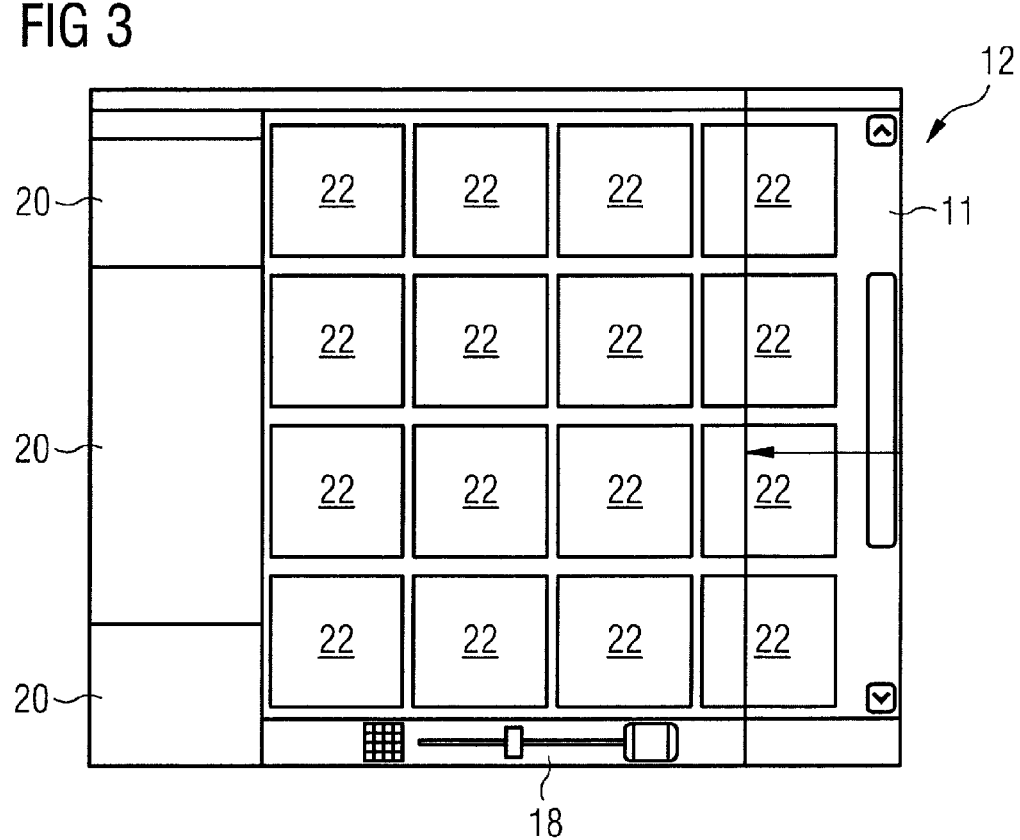
FIG. 3 is a schematic illustration of a window portion of a computer display before horizontal downsizing according to a preferred embodiment of the present invention.

FIG. 3 shows the window 12 before the user makes a change to decrease the horizontal sizing of the window. A vertical line depicted in a region to the right in FIG. 3 that represents a new right border or edge of the window 12. An arrow pointing in a direction to the left represents the horizontal scaling or downsizing action to be taken. The arrow extends from the original right side edge of the window 12 to a line indicating a new location of the right side edge after the change. Based on the user-selected size modification of the window 12, a display calculation process according to the invention starts and the display of the thumbnail objects 22 is modified based on the new calculation of the object size. After having completed the calculation, the thumbnail objects 22 are depicted in a new or adapted representation of the window 12.

Figure 4:
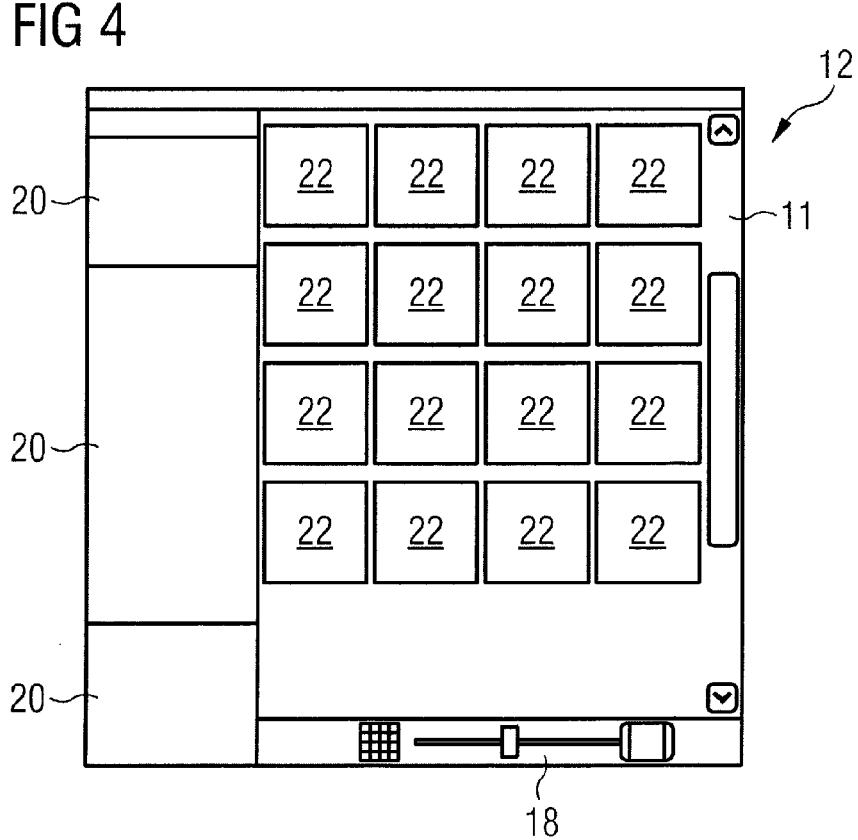
FIG. 4 is a schematic illustration of the window of FIG. 3 after horizontal downsizing according to a preferred embodiment of the present invention.

The adapted representation of the window 12 is shown in FIG. 4. FIG. 4 shows the window 12 after the horizontal downsizing indicated in FIG. 3 has been performed. By comparing the drawings it is apparent that the object size of the thumbnail objects 22 has been changed, in particular the size of the thumbnail objects has been diminished, in dependence on the horizontal downsizing of the window 12. A general display pattern which has been selected by using the slider control 18 has been maintained. Thus, sixteen thumbnail objects 22 are still shown in the selected layout.

In particular, the thumbnail objects 22 of FIG. 3 are of a size to permit 16 such objects to be displayed in the window 12 in a four by four arrangement. The downsizing, or reduction in size, of the window results in a smaller dimension for display of the thumbnail objects in the new window, but the four by four arrangement is to be maintained without obscuring any of the thumbnails by the edge of the window. The thumbnails are thus reduced in size generally in proportion to the reduction of the window. The new smaller thumbnails fit into the new smaller window in the same four by four arrangement. The thumbnails of the illustrated embodiment are square and the square shape is maintained after reduction. In general, regardless of the shape of the thumbnail object the proportions of the thumbnail objects is maintained during resizing. By maintaining the same arrangement after resizing, the position of any thumbnail object in the arrangement is maintained so that the resized display does not result in some thumbnail objects moving from one position, for example the second row, to another position, for example in the third row.

Figure 5:
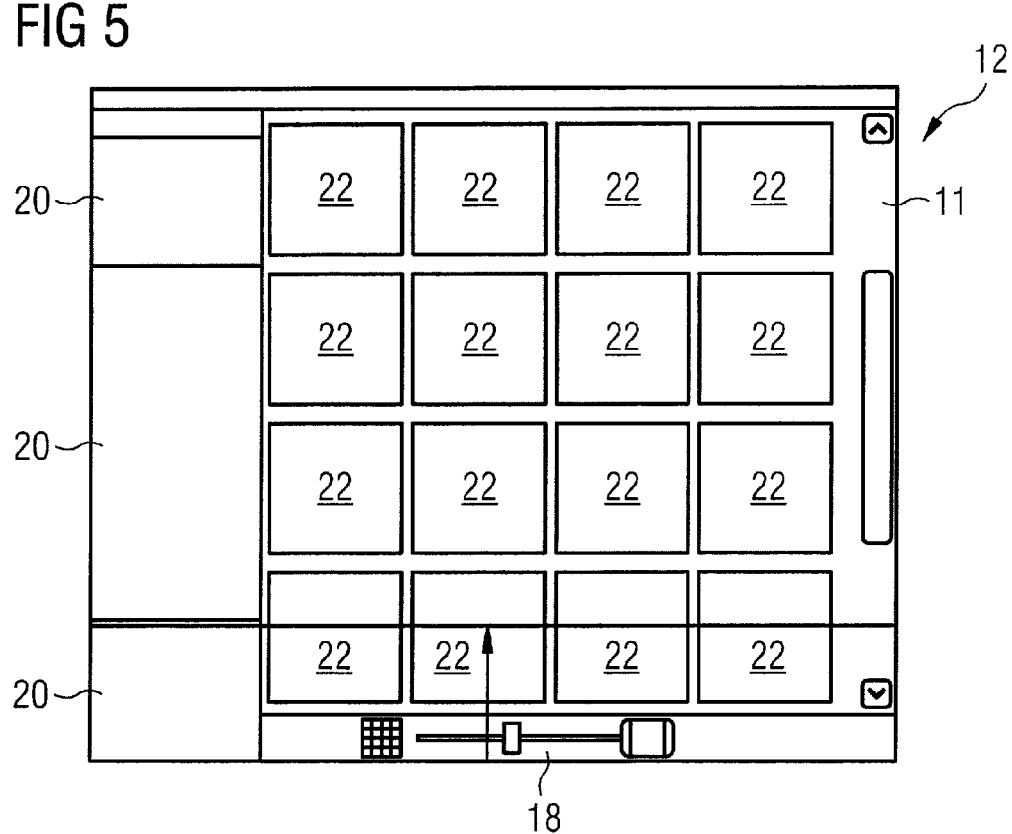
FIG. 5 is a schematic illustration of a window portion of a computer display before vertical downsizing according to a preferred embodiment of the present invention.

FIG. 5 shows a browser window 12 before vertical downsizing of the window. In FIG. 5, a horizontal line is shown to represent a future bottom edge or border of the new window 12 after rescaling. An upwardly directed arrow represents a vertical scaling or downsizing action. After the vertical downsizing of the window 12, the display of window 12 is calculated (possibly again). According to the new calculation, a new representation of the window 12 will be displayed on the monitor 10.

Figure 6:
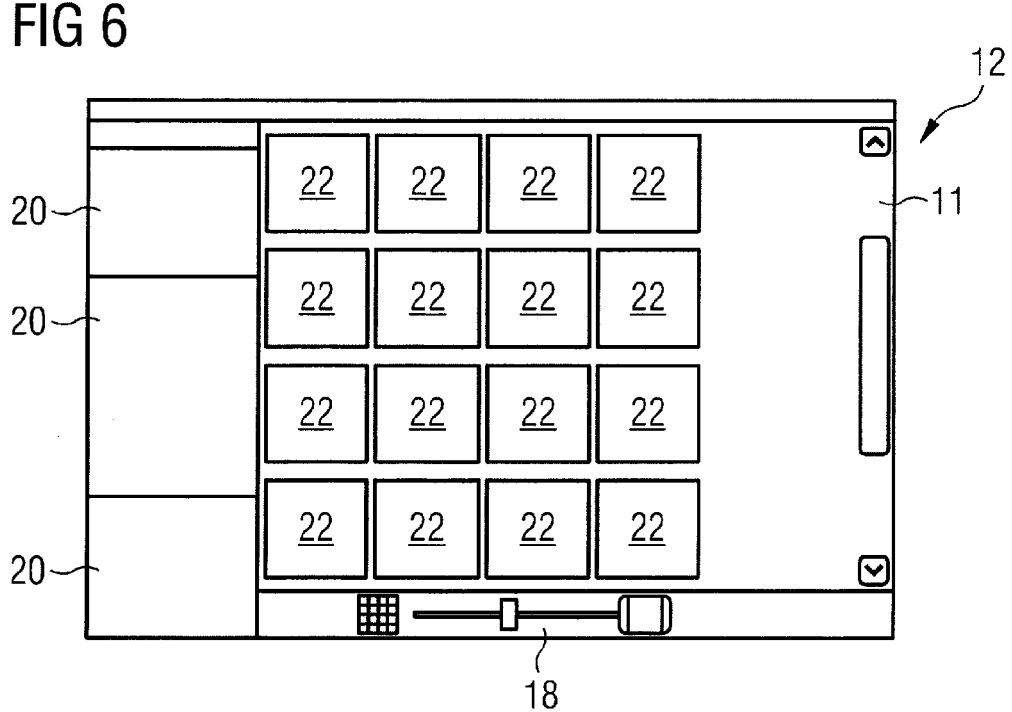
FIG. 6 is a schematic illustration of the window of FIG. 5 after vertical downsizing according to a preferred embodiment of the present invention.

This new representation of the window 12 after vertical downsizing is shown in FIG. 6. FIG. 6 shows that the browsing window 12 after vertical downsizing maintains the selected layout pattern (4×4 thumbnail layout). FIG. 6 shows the result of the action indicated in FIG. 5. In particular, the reduced size window has thumbnails 22 that have been reduced in size yet maintain the same arrangement. The reduction in the size of the thumbnails maintains the proportions of the original thumbnail objects and maintains each object in the same position within the arrangement.

Figure 7:
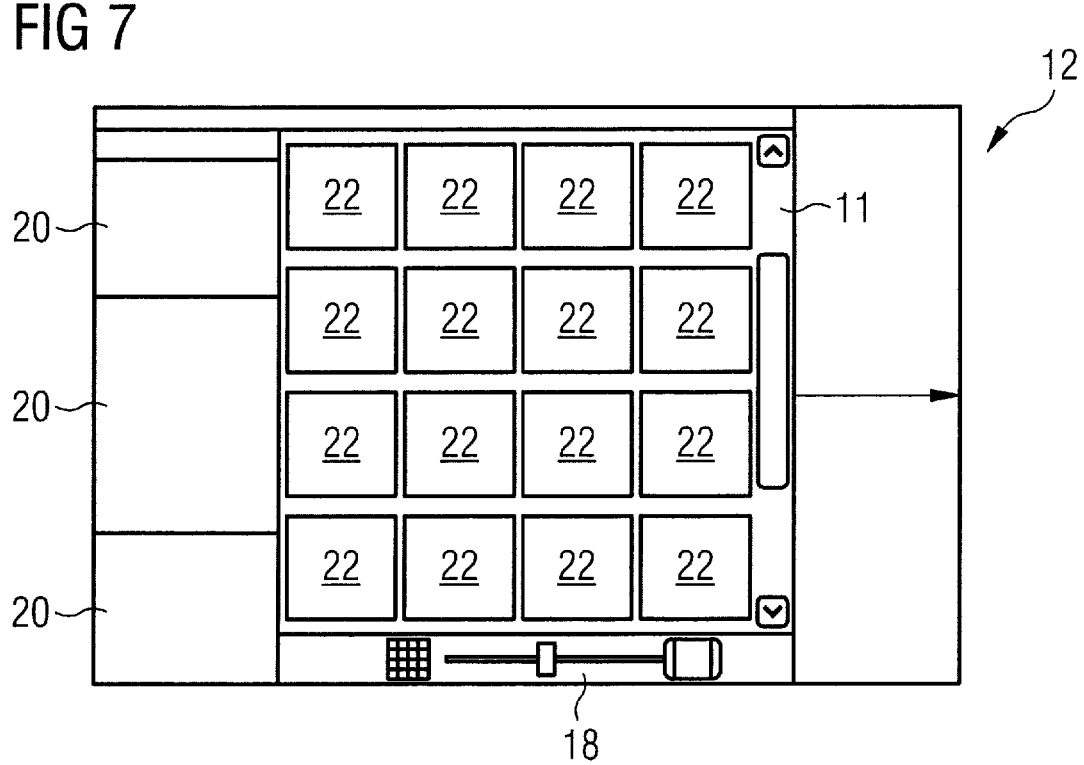
FIG. 7 is a schematic illustration of a window portion of a computer display before horizontal enlargement according to a preferred embodiment of the present invention.

FIG. 7 shows the browsing window 12 before a horizontal enlargement action by the user. In FIG. 7 the horizontal enlargement is indicated by the arrow directed to the right from the right side edge of the original window to a new right side edge of the enlarged window.

Figure 8:
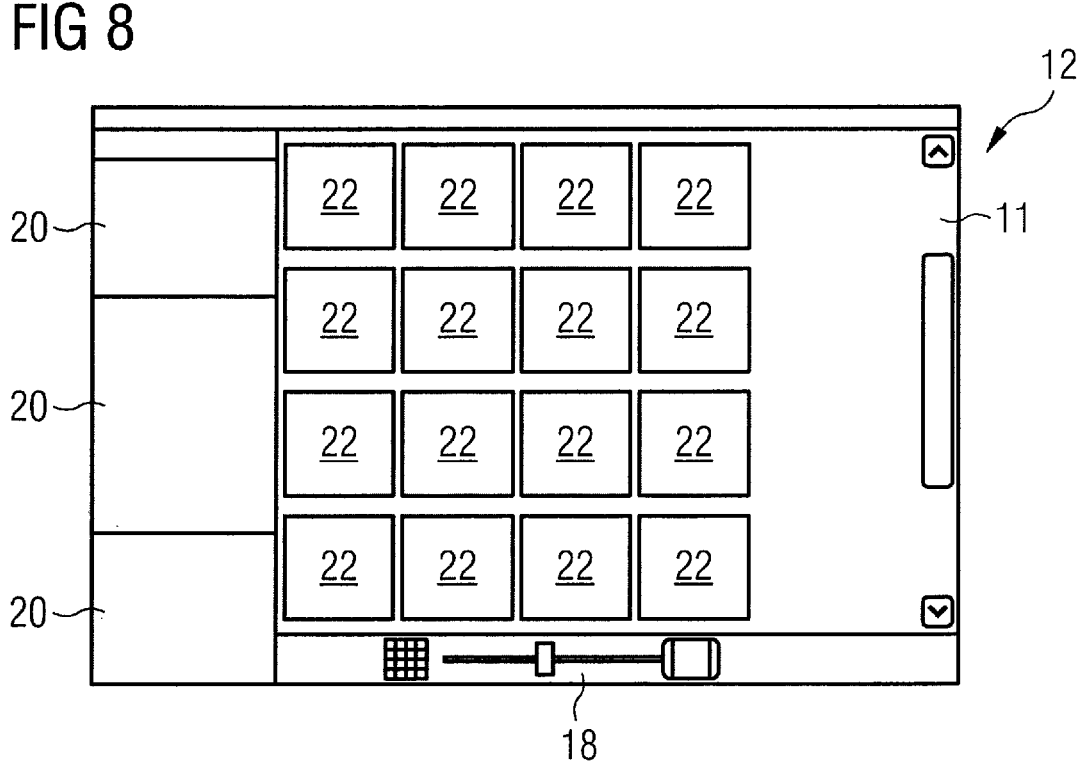
FIG. 8 is a schematic illustration of the window of FIG. 7 after horizontal enlargement according to a preferred embodiment of the present invention.

In FIG. 8 is shown the result of the horizontal enlargement indicated in FIG. 7. FIG. 8 shows the new window 12 after the enlargement action by moving the right side edge has been moved to the right. The newly calculated thumbnail objects 22 are displayed in the calculated size according to the horizontal enlargement action. The new window has not been increased in the vertical dimension and no enlargement of the thumbnails is possible while maintaining the arrangement and the proportions of the thumbnails. Thus, the newly calculated thumbnail size is the same as the original thumbnail size. It is foreseeable that instead of a calculation of the thumbnail size being performed, a check is carried out as to whether the re-sized window would require a thumbnail size calculation.

Figure 9:
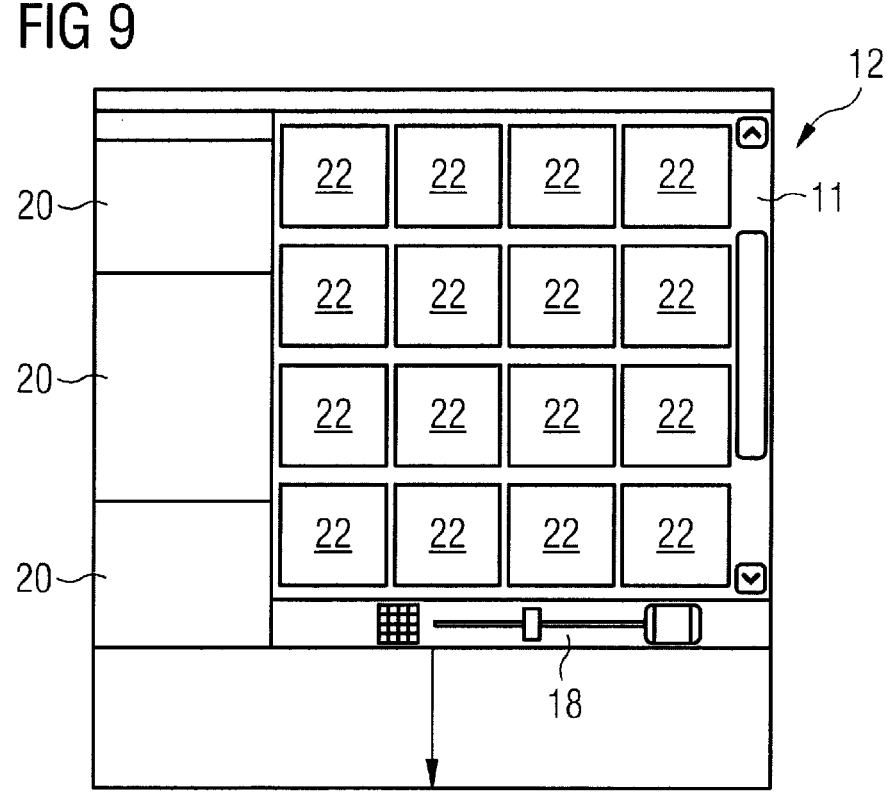
FIG. 9 is a schematic illustration of a window portion of a computer display before vertical enlargement according to a preferred embodiment of the present invention.

FIG. 9 shows the browsing window 12 before a vertical enlargement action by the user. The vertical enlargement is indicated by the arrow directed downwards. The original bottom edge is shown and the arrow extends to the new bottom edge of the window after the enlargement action by the user.

The vertically enlarged window 12 is shown in FIG. 10. Thus, FIG. 10 shows the window 12 after the vertical enlargement action indicated in FIG. 9, while maintaining the original layout pattern. The thumbnail objects 22 have not been changed in size, although according to one embodiment a calculation of thumbnail object sizes is carried out. In the alternative embodiment, the determination that no change is thumbnail size is needed is performed without recalculating the size.

Pairs of FIGS. 3 & 4, FIGS. 5 & 6, FIGS. 7 & 8 and FIGS. 9 & 10 demonstrate that after a modification of the window size from its original size, the new representation of the window 12 includes free space. The free space is the result of the adapted calculation of the thumbnail object size (in two dimensions), whereas the change in the window size has been made only along one axis of the window 12 (either vertical or horizontal). However, if the window size change is made with respect to both axes, typically either no free space will be generated or less free space will be generated, because the display pattern is based on thumbnail objects 22 of fixed proportions, for example square thumbnail objects and the resized thumbnail objects fill some or all of the possible new free space.

It is also possible that the resizing of the window may result in a reduction in free space. For example, if the original window has free space along the bottom and the window is reduced in size in the vertical direction, some of that free space may be no longer be present in the resized window, regardless of whether the window reduction also results in a reduction in the thumbnail objects being reduced. The same applies for horizontal resizing. Similarly, if the original window has free space along the bottom and a horizontal resizing of the window to a bigger size is performed, the recalculation of the thumbnail objects may result in an increase in size of the thumbnail objects while maintaining the same arrangement. This could result in some of the free space at the bottom of the window being taken up by the new, larger thumbnails. The same applies for vertical resizing.

After a modification of the size of the window 12, the sizes of the thumbnail objects are newly calculated. According to a preferred embodiment of the present invention, the size of the thumbnail objects 22 can be diminished or be enlarged, while maintaining the original display pattern.

According to a preferred embodiment, an initial size of the window 12 is predefined. Preferably, the initial size of the window, the size that is displayed first, is a full screen size that is determined according to the respective monitor 10. Alternatively, ½, ¼, ⅛ screen size displays are definable. In response to a user input, the initial size is user-selectable as a pre-defined size in a preparation phase. According to a preferred embodiment, the application automatically launches in two different sizes on the screen 10 in order to adjust to different monitor resolutions (examples of monitor resolutions include 1024×768 pixels and 1280×1024 pixels). Additionally, other predefinitions can be made, for example if the monitor 10 is a large-format screen with a one meter height which is to be used in specific medical cases, appropriate predefined arrangements are provided. Manual resizing of the window 12 is generally carried out using the mouse or other pointer to drag the resizer handle at the bottom right corner of the window 22 or one of the window borders (left, right, top or bottom).

According to yet another embodiment of the present invention, it is possible to modify the display pattern and/or the window size. The modifications can also be made during displaying of the thumbnail objects 22. In case any modifications are detected, the calculation of an adapted display is triggered automatically and a new representation of the window 12 is displayed according to the updated parameters (window size, layout pattern).

According to yet another embodiment of the present invention the following parameters are user-selectable: a) the display pattern, and b) the window size. Accordingly, the object size and number of objects is controlled separately. In a preferred embodiment the parameters of: a) object size (the size of the thumbnail objects 22) and b) the amount or number of thumbnail objects 22 being displayed, can be controlled independently. A change of the display pattern may lead to a change of the number of objects 22 to be displayed and further may lead to a change of size of the objects 22. A change of the window size or of the frame size may lead to a change of the size of the thumbnail objects 22, while maintaining the display pattern as a constant arrangement, so long as the user has not selected a different display pattern. Otherwise, both the window size and the display pattern parameters can be modified: the user is able to modify the display pattern and the window or frame size.

After having detected those parameters, which are user selectable (namely the layout pattern and the window size or the frame size respectively) the number of thumbnail objects 22 to be displayed and the size of the thumbnail objects 22 are calculated automatically. According to a preferred embodiment the size of the thumbnail objects 22 cannot be adjusted manually by user interaction but is calculated automatically.

Figure 12:
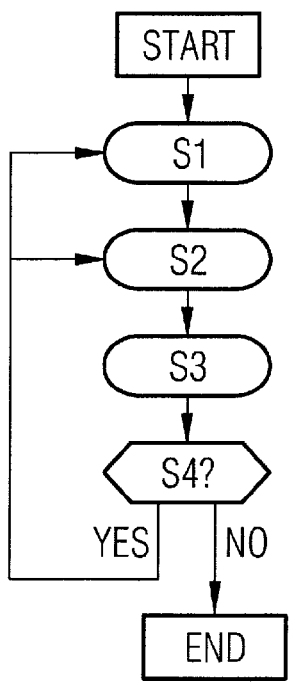
FIG. 12 is a flow chart of the method according to a preferred embodiment of the present invention.

With respect to FIG. 12, the invention is described on a functional level. The process flow chart illustrates the steps that are being performed, for example, when a user starts and then uses the image display program on a computer display or a display of other technical equipment.

After starting the application, in a first step indicated with reference character S1, a display pattern is user-selected. The application may present a plurality of display patterns from which the user may select.

In a second step indicated as reference character S2, a calculation of object size is performed. The calculation is based on the user-selected display pattern from step S1 and according to the detected window size. The window size might be pre-defined (and is thus already set and is not user selected) or might be user-modified, as described above.

In a third step S3, the thumbnail objects 22 are displayed in the calculated size of the objects 22 in the window 12.

In a forth step S4, the system detects whether or not the window size and/or the display pattern has been modified. In the flow chart of FIG. 12, this forth step S4 is depicted after the displaying action of step S3. However, it is also possible to execute this forth step S4 continuously or at least during displaying of the objects in the window in step S3. In other words the detection step in essence asks the question, "Has there been a modification with respect to window or frame size or display pattern?" This inquiry might also be executed during launching and running the application and also during displaying the thumbnail object 22 in step S3. If no such modification is detected, the method or process ends and otherwise (if a modification of the window size or of the display pattern has been detected) there are two possibilities for the further running of the process. A first possibility is that the method starts again or continues at the first step S1, so that the user has the possibility to once more select the display pattern. Second, it is possible that the method starts at the second step S2 for a new calculation of object size.

In the following an exemplary computation of the object size is given.

Input parameters of the computation are:
h1—height of window for displaying images
w1—width of window for displaying images
n1—number of images per column
n2—number of images per row
m1—upper margin
m2—vertical space between two rows
m3—minimum bottom margin
m4—left margin
m5—horizontal space between two columns
m6—minimum right margin.

Intermediate parameters used in calculation of the present method include:

h2—available space for images (without upper and lower margins and spaces between rows). The parameter h2 is calculated according to the following formula:

$$h2=h1-m1-m3-(n1-1)*m2$$

w2=available space for images (without left and right margins and spaces between columns). The parameter w2 is calculated according to the following formula:

$$w2=w1-m4-m6-(n2-1)*m5$$

A final computation may be based on the following formulas:

$$x = \text{edge length of object}$$

x=y (when image objects are squares), or otherwise according to object proportion $$x=\text{MINIMUM}(h2/n1, w2/n2)$$

A major advantage of the present invention is that a user need not be concerned with the size of the thumbnail object 22 to be displayed. The size adaption of the thumbnail object 22 takes place automatically. Further, there is no resorting or rearranging of thumbnail objects 22, even in the case where the window size has been modified.

The presented description of illustrated embodiments of the invention is not intended to be exhaustive or to limit the invention to precise forms disclosed. While specific embodiments of, and examples for, the invention are described herein for illustrative purposes various equivalent modifications are possible within the scope of the invention and can be made without deviating from the scope of the invention.

For example, to some extent the description is based on a user performing a browsing of the thumbnail objects 22. Alternatively, the displaying step according to the invention might also be used for other purposes than browsing.

Further, the method might be implemented in software, in coded form to be used in connection with a computer. Alternatively, it is possible to implement the method according to the invention in hardware or hardware modules. The hardware modules are then adapted to perform the functionality of the steps of the method. Furthermore, it is possible to have a combination of hardware and software modules.

For example, the computer program product may be implemented in or control a monitor to display a set of thumbnail objects on a window of the monitor in a non-overlapping manner, a display pattern module to determine a display pattern for the objects, wherein the display pattern includes a number of objects, a window size module to determine a size of the window, a calculation module to automatically calculate a size of the object according to the window size module and according to the display pattern module, a display to display the objects for browsing according to the determined display pattern of the display pattern module and according to the determined window size of the window size module in the calculated size according to the calculation module.

These and other modifications can be made to the invention with regard of the above detailed description. The terms used in the following claims should not be construed to limit the invention to the specific embodiments disclosed in the specification and the claims. Rather, the scope of the invention is to be determined entirely by the following claims, which are to be construed in accordance with established doctrines of claim interpretation.

Although other modifications and changes may be suggested by those skilled in the art, it is the intention of the inventors to embody within the patent warranted hereon all changes and modifications as reasonably and properly come within the scope of their contribution to the art.

We claim:

1. A method for browsing individual medical thumbnail objects of fixed proportions on a monitor wherein the thumbnail objects displayed in an original size window are to be displayed in a changed size window on the monitor in a non-overlapping non-obscuring manner, comprising the steps of:

providing a computer with software for displaying the thumbnail objects on said monitor as a graphical user interface;

with said software determining window display dimensions of the original size window, determining said fixed proportions for each of the individual thumbnail objects, determining a display pattern of said thumbnail objects displayed in said original size window, determining a number of the thumbnail objects in said pattern, determining an amount of space between the individual thumbnail objects, and determining a margin between the displayed pattern and edges of the original size window;

automatically calculating with said software respective thumbnail object display dimensions of each of the individual thumbnail objects based on said fixed proportions of the thumbnail objects, based on said dimensions of the original size window, based on said pattern, based on said number of thumbnail objects within said pattern, based on said amount of space between the thumbnail objects, and based on said margin;

upon receipt of a user input, with said software scaling window display dimensions for said changed size window, automatically resizing the thumbnail objects while retaining said fixed proportions of the thumbnail objects, retaining said same display pattern, and retaining the same number of original thumbnail objects in said display pattern; and displaying, in said changed size window in said non-overlapping and non-obscured manner, the resized thumbnail objects with the same display pattern, with the same number of individual thumbnail objects in said display pattern, and with said same fixed proportions of the individual thumbnail objects.

2. The method of claim 1 wherein said display pattern is triggered by a user input from a pre-defined set of display patterns.

3. The method of claim 1 wherein the display pattern is determined based on a pre-defined user-selectable matrix-like grid structure set by a slider as an element of the graphical user interface.

4. The method of claim 1 including the steps of determining a type of data to be displayed, and automatically determining the display pattern based on pre-definable rules.

5. A system for browsing individual medical thumbnail objects of fixed proportions, comprising:
 a processor that executes computer executable instructions;
 a monitor as a graphical user interface operable by the processor and wherein individual thumbnail objects displayed in an original size window are to be displayed in a changed size window on the monitor in a non-overlapping non-obscuring manner;
 said processor, by executing said executable instructions, performing the steps of:
 determining widow display dimensions of the original size window, determining said fixed proportions for each of the individual thumbnail objects, determining a display pattern of said thumbnail objects displayed in said original size window, determining a number of the thumbnail objects in said pattern, determining an amount of space between the individual thumbnail objects, and determining a margin between the displayed pattern and edges of the original size window;
 automatically calculating respective thumbnail object display dimensions of each of the individual thumbnail objects based on said fixed proportions of the thumbnail objects, based on said dimensions of the original size window, based on said pattern, based on said number of thumbnail objects within said pattern, based on said amount of space between the thumbnail objects, and based on said margin;
 upon receipt of a user input, scaling window display dimensions for said changed size window, automatically resizing the thumbnail objects while retaining said fixed proportions of the thumbnail objects, retaining said same display pattern, and retaining the same number of original thumbnail objects in said display pattern; and
 displaying, in said changed size window in said non-overlapping and non-obscured manner, the resized thumbnail objects with the same display pattern, with the same number of individual thumbnail objects in said display pattern, and with said same fixed proportions of the individual thumbnail objects.

6. A non-transitory computer-readable storage medium having stored thereon computer program code with instructions that are executable on a computer for browsing individual medical objects of fixed proportions on a monitor wherein the thumbnail objects displayed in an original size window are to be displayed in a changed size window on the monitor in a non-overlapping non-obscuring manner, the computer program code, when the storage medium is loaded in the computer, causes the computer to perform the steps of:
 determining widow display dimensions of the original size window, determining said fixed proportions for each of the individual thumbnail objects, determining a display pattern of said thumbnail objects displayed in said original size window, determining a number of the thumbnail objects in said pattern, determining an amount of space between the individual thumbnail objects, and determining a margin between the displayed pattern and edges of the original size window;
 automatically calculating respective thumbnail object display dimensions of each of the individual thumbnail objects based on said fixed proportions of the thumbnail objects, based on said dimensions of the original size window, based on said pattern, based on said number of thumbnail objects within said pattern, based on said amount of space between the thumbnail objects, and based on said margin;
 upon receipt of a user input, scaling window display dimensions for said changed size window, automatically resizing the thumbnail objects while retaining said fixed proportions of the thumbnail objects, retaining said same display pattern, and retaining the same number of original thumbnail objects in said display pattern; and
 displaying, in said changed size window in said non-overlapping and non-obscured manner, the resized thumbnail objects with the same display pattern, with the same number of individual thumbnail objects in said display pattern, and with said same fixed proportions of the individual thumbnail objects.

* * * * *